United States Patent [19]

Egli

[11] 4,395,544
[45] Jul. 26, 1983

[54] 4-HALO-5-FORMYL THIAZOLES

[75] Inventor: Robert Egli, Rheinfelden, Switzerland

[73] Assignee: Sandoz Ltd., Basel, Switzerland

[21] Appl. No.: 264,019

[22] Filed: May 15, 1981

Related U.S. Application Data

[63] Continuation-in-part of Ser. No. 144,383, Apr. 28, 1980, abandoned.

[30] Foreign Application Priority Data

May 3, 1979 [CH] Switzerland .......................... 4142/79

[51] Int. Cl.³ ............................................ C07D 277/28
[52] U.S. Cl. .................................... 542/413; 542/417; 542/421; 542/400; 542/429; 542/427; 542/414; 542/441; 542/445; 542/446; 542/453; 542/468; 542/476; 542/472; 548/133; 548/190; 548/193; 548/194; 548/195; 548/196; 548/367; 546/209
[58] Field of Search ............... 548/190, 193, 194, 195, 548/196, 133, 367; 542/413, 417, 441, 445, 421, 472, 446, 427, 400, 476, 453, 429, 468, 414; 546/209

[56] References Cited

U.S. PATENT DOCUMENTS

| | | | |
|---|---|---|---|
| 3,444,178 | 5/1969 | Bachman | 548/194 |
| 3,547,917 | 12/1970 | Kulka et al. | 548/194 |
| 3,573,289 | 3/1971 | Straley et al. | 548/194 |
| 3,829,410 | 8/1974 | Fisher et al. | 548/199 |
| 4,165,377 | 8/1979 | Jones et al. | 548/194 |
| 4,165,378 | 8/1979 | Gilman et al. | 548/194 |

FOREIGN PATENT DOCUMENTS

| | | |
|---|---|---|
| 2729914 | 1/1978 | Fed. Rep. of Germany . |
| 2818101 | 11/1978 | Fed. Rep. of Germany . |
| 136147 | 6/1979 | German Democratic Rep. . |
| 2003495 | 3/1979 | United Kingdom . |

OTHER PUBLICATIONS

Andreani et al., Current Abstracts of Chemistry, vol. 71 (1978) II 277993.

Primary Examiner—Arthur P. Demers
Attorney, Agent, or Firm—Gerald D. Sharkin; Richard E. Vila; Thomas C. Doyle

[57] ABSTRACT

The present invention relates to compounds obtained by condensing a compound of formula I,

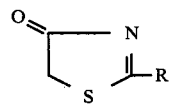

I or a salt thereof,
in which R is a primary, secondary or tertiary amino group,
with a Vilsmeier reagent,
and derivatives of such aldehydes.

29 Claims, No Drawings

4-HALO-5-FORMYL THIAZOLES

The present application is a continuation-in-part of application Ser. No. 144,383, filed Apr. 28, 1980 and now abandoned.

The present invention relates to thiazole compounds and the process for their production.

It has been found that novel 4-halo-5-formyl-thiazoles are formed by condensing 4-oxy-thiazoles with a Vilsmeier reagent, for example, one based on phosphorousoxychloride and an amide.

More particularly, the present invention provides compounds obtained by condensing a compound of formula I,

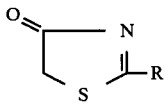

or a salt thereof,
in which R is a primary, secondary or tertiary amino group,
with a Vilsmeier reagent,
and derivatives of such aldehydes.

The preferred Vilsmeier reagent is that from phosphorousoxychloride and dimethylformamide.

Preferred compounds according to the present invention are those of formula II,

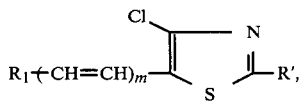

in which $R_1$ is —CHO, —CH=$CR_4R_5$, —CN, —CH=NOH, —$CH_2OR_6$, —CH=N-$NHR_7$,

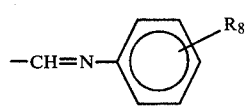

—CH(OH)CN or an open chain or cyclic acetal or thioacetal group,

R' is a primary, secondary or tertiary amino or an imino group, with the provisos that R' is primary amino when $R_1$ is other than —CHO or —CH=$CR_4R_5$ and R' is a secondary or tertiary amino group when $R_1$ is —CH=$CR_4R_5$, either, $R_4$ is hydrogen, cyano, alkylcarbonyl, benzoyl, alkylsulphonyl, phenylsulphonyl, alkylaminocarbonyl, dialkylaminocarbonyl, phenylaminocarbonyl, N-alkyl-N-phenylaminocarbonyl, aminocarbonyl, aminocarbonylaminocarbonyl, piperidinylcarbonyl, aminothiocarbonyl, benzimidazolyl-2 or —COOB, in which B is hydrogen; $C_{1-10}$alkyl; $C_{5-7}$cycloalkyl; $C_{1-6}$alkyl substituted by up to three substituents selected from the group consisting of chlorine and bromine; $C_{1-6}$alkyl substituted by up to two substituents selected from the group consisting of chlorine, bromine, hydroxyl, cyano, phenoxy, alkoxy, carboxy, alkoxycarbonyl, alkylcarbonyloxy, alkoxycarbonyloxy, alkylaminocarbonyloxy, aminocarbonyl, alkylaminocarbonyl, phenylaminocarbonyl, benzyloxycarbonyl, and phenyl, in which the phenyl ring is optionally substituted by 1 or 2 substituents selected from chlorine bromine and nitro, with the proviso that when such alkyl is substituted by a group containing a benzene ring it is monosubstituted and any substituted alkyl is free from acetal groups; or B is $C_{3-6}$alkenyl optionally substituted by chlorine or bromine; or is alkynyl.

and $R_5$ is hydrogen, cyano, alkoxycarbonyl, nitro or 3-di-cyanomethylene-5-5-dimethylcyclohexen-1-yl with the proviso that when $R_5$ is the latter $R_4$ is hydrogen and when $R_5$ is nitro $R_4$ is hydrogen, methyl or ethyl, or $R_4$ and $R_5$ together form a 5- or 6-membered carbocyclic or heterocyclic ring system, $R_6$ is hydrogen, alkyl, alkylcarbonyl or benzyl in which the benzene ring is optionally substituted by up to two substituents selected from chlorine, bromine and nitro, $R_7$ is hydrogen, alkyl, aminocarbonyl, amino thiocarbonyl or phenyl which is optionally substituted by 1 or 2 substituents selected from the group consisting of chlorine, bromine and nitro, $R_8$ is hydrogen, chlorine, bromine, methyl, $C_{1-2}$alkoxy, carboxyl, alkoxycarbonyl, cyano or nitro, p1 m is 0 or 1, and any alkyl and alkoxy groups or moieties in such compounds contain 1 to 4 carbon atoms and any alkenyl or alkynyl groups or moieties 3 to 4 carbon atoms, except when otherwise stated.

Preferred groups R', are those of formula $$-NR_2R_3$$

in which either
$R_2$ is hydrogen; $C_{1-10}$alkyl; $C_{2-3}$alkyl substituted by hydroxy, cyano, chlorine, bromine, alkyl-$C_{1-2}$carbonyl, alkoxy-$C_{1-4}$carbonyloxy, alkyl$C_{1-4}$carbonyloxy, alkylamiocarbonyloxy, dialkylaminocarbonyloxy, alkoxy$C_{1-4}$carbonyl, phenylaminocarbonyloxy or N-alkyl-N-phenylaminocarbonyloxy with the proviso that such substituted alkyl radicals are free from acetal groups; phenyl optionally substituted by 1 or 2 substituents selected from chlorine, bromine, methyl and nitro; alkenyl; dicyanoalkenyl; cyclohexyl; or naphthyl, and $R_3$ has one of the significances of $R_2$ with the provisos that when one of $R_2$ and $R_3$ is naphthyl the other has a significance other than naphthyl or phenyl, and when one of $R_2$ and $R_3$ is dicyanoalkenyl the other is hydrogen, or, $R_2$ and $R_3$ together with the nitrogen atom form a 5- or 6-membered heterocyclic ring, in particular piperidine, piperazine or morpholine, or $R_2$ and $R_3$ together form a group of formula $$=CH-(CH=CH)_{m'}NR_{10}R_{11}$$

in which either,
$R_{10}$ is hydrogen or alkyl, and
$R_{11}$ is hydrogen, alkyl or phenyl,
or, $R_{10}$ and $R_{11}$ together with the N-atom form piperidine,
m' is 0 or 1, and
any alkyl groups and moieties contain 1 to 4 carbon atoms and any alkenyl group 3 to 4 carbon atoms except where otherwise stated.

When $R_4$ and $R_5$ together form a carbocyclic or heterocyclic ring system, preferred rings are

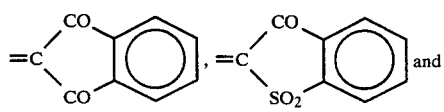, 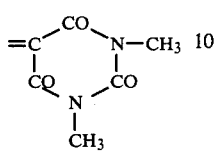

The preferred $C_{1-4}$alkyl groups or moieties in significances for $R_4$ are those which contain 1 or 2 carbon atoms. The preferred alkenyl and alkynyl moieties are those which contain 3 or 4 carbon atoms.

$R_2$ is preferably $R_2'$, where $R_2'$ is hydrogen, $C_{1-4}$alkyl, hydroxyethyl, cyanoethyl or phenyl and $R_3$ is preferably $R_3'$, where $R_3'$ is hydrogen, $C_{1-4}$alkyl, allyl, cyclohexyl, or naphthyl, or $R_2'$ and $R_3'$ form a group of formula $=CH(CH=CH)_{m'}NR_{10}R_{11}$, where $R_{10}$ and $R_{11}$ are $C_{1-4}$alkyl, especially methyl, preferably with $m'=0$. Preferably when $R_3'$ is cyclohexyl or phenyl $R_2'$ is other than phenyl and when $R_3'$ is naphthyl $R_2'$ is preferably hydrogen.

$R_1$ is preferably $R_1'$, where $R_1'$ is —CHO, —CH=$CR_4R_5$, —CH=NOH or CN, especially —CHO, —CH=$CR_4'R_5'$, CN or —CH=NOH.

$R_4$ is preferably $R_4'$, where $R_4'$ is cyano; benzoyl; methylsulphonyl; phenylsulphonyl; methyl or ethylaminocarbonyl; phenylaminocarbonyl; aminocarbonyl; aminocarbonylaminocarbonyl; piperidinylcarbonyl; benzimidazolyl-2 or —COOB', where B' is $C_{1-10}$alkyl, cyclohexyl, $C_{1-6}$alkyl substituted by up to two substituents selected from the group consisting of chlorine, bromine, hydroxy, cyano, $C_{1-2}$alkoxy, carboxy, alkoxy($C_{1-2}$)carbonyl, alkyl($C_{1-2}$)carbonyloxy, $C_{1-2}$alkoxycarbonyloxy, $C_{1-2}$alkylaminocarbonyloxy, aminocarbonyl, phenylaminocarbonyl, benzyloxycarbonyl, phenyl, chlorophenyl, nitrophenyl, with the proviso that when such alkyl is substituted by a group containing a benzene ring it is monosubstituted and any substituted alkyl is free from acetal groups; or B' is alkenyl optionally substituted by chlorine or bromine or is alkynyl.

$R_5$ is preferably $R_5'$, where $R_5'$ cyano, nitro or 3-dicyanomethylene-5,5-dimethylcyclohexen-1-yl with the proviso that when $R_5'$ is any one of the latter two significances $R_4$ is hydrogen.

More preferably $R_1$ is $R_1''$, where $R_1''$ is —CHO, or —CH=$CR_4R_5$ especially —CHO or CH=$CR_4'R_5'$. Most preferably $R_1$ is $R_1'''$, where $R_1'''$ is —CHO or —CH=C(CN)$R_4''$ where $R_4''$ is cyano, alkoxy($C_{1-6}$)carbonyl, benzoyl, cyclohexyloxycarbonyl, $C_{3-4}$-alkenyloxycarbonyl, chloro- or bromo-$C_{3-4}$alkenyloxycarbonyl or alkoxy($C_{1-6}$)carbonyl in which the alkyl group is substituted by up to two substituents selected from the group consisting of chlorine, bromine, hydroxyl, phenyl, carboxy, alkoxy$C_{1-2}$carbonyl, alkyl($C_{1-2}$)carbonyloxy, $C_{1-2}$alkylaminocarbonyloxy, alkoxy$C_{1-2}$carbonyloxy, with —CHO being most preferred for $R_1$.

Preferred compounds of formula II are those in which $R_1$ is $R_1'$, $R_2$ is $R_2'$, $R_3$ is $R_3'$ especially those where $R_4$ and $R_5$ are $R_4'$ and $R_5'$.

More preferred compounds of formula II are those in which $R_1$ is $R_1''$, $R_2$ is $R_2'$, $R_3$ is $R_3'$ especially those where $R_5$ is cyano and $R_4$ is $R_4''$.

Most preferred compounds of formula II are those in which $R_1$ is $R_1'''$, $R_2$ is $R_2'$ and $R_3$ is $R_3'$, especially those where m is 0.

The reaction of the compounds of formula I with a Vilsmeier reagent may be carried out in accordance with known methods. In general at least 2 mols, and when R is a primary amino group, preferably at least three mols Vilsmeier reagent are employed. When a primary amine of formula I is employed, the =CH(CH=CH)$_{m'}$NR$_{10}$R$_{11}$ group attached to the 2-position can be hydrolytically split off, e.g. by heating the acid solution, when compounds of formula II wherein $R_2$ and $R_3$ are both hydrogen are desired.

Suitable amides for the Vilsmeier reagent include formamide, dimethylformamide, N-methylformanilide, formylpiperidine and vinyl-group-containing formyl compounds, for example $(CH_3)_2N$—CH=CH—CHO, with dimethylformamide being especially preferred. The preferred acid halides for the Vilsmeier reagent are the acid chlorides, especially phosphorousoxychloride. When a vinyl-group containing Vilsmeier agent is employed compounds of formula II in which m and m' are 1 are obtained.

The formyl group in the compounds of formula II may be converted to any of the other significances for $R_1$ by known methods, for example condensation with a hydroxylamine and optionally with acylation to obtain compounds where $R_1$ is cyano; reaction with hydrazine or a derivative thereof; preparation of a cyanohydrin; preparation of Schiff bases, Knoevenagel, reduction to form an alcohol optionally with esterification or etherification etc.

It will be appreciated that hydrogen atoms on the amino group in the 2-position may be replaced by a protecting group before reacting the formyl compounds further and said protecting group can be subsequently split off.

The compounds of formula I are known or may be prepared by known methods from available starting materials.

The novel compounds according to the invention are useful as dyestuffs and/or as intermediates for the preparation of dyestuffs. Compounds which have a secondary or tertiary amino group in the 2-position and a formyl group in the 5-position can be reacted with compounds having an activated methylene group, for example malonic acid derivatives in accordance with the Knoevenagel reaction to obtain a compound of formula VI

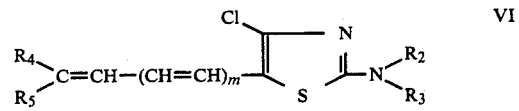

in which
$R_2$ to $R_5$ are as defined above and at least one of $R_2$ and $R_3$ is other than hydrogen,
which compounds of formula VI are useful as disperse dyestuffs for dyeing or printing hydrophobic, high-molecular weight, synthetic or semi-synthetic organic substrates, for example cellulose 2½ acetate, cellulose triacetate, polyesters and synthetic polyamides. The dyeings obtained have good fastness, and the dyestuffs have notable buildup power on polyester and give intense dyeings.

Compounds having a primary amino group in the 2-position are useful as dyestuff diazo components.

The following Examples further serve to illustrate the invention. In the Examples all parts and percentages are by weight and the temperatures are in degrees Centigrade.

EXAMPLE 1

46 Parts phosphorousoxychloride are added at 0° to 5° to 73 parts N,N-dimethylformamide. 15.2 Parts 2-aminothiazoline-4-one-hydrochloride are added portionwise at 0° to 5° to the colourless solution. The cooling bath is removed and the mixture is heated to 70°. After 14 hours stirring the mixture is allowed to cool and is poured carefully onto a mixture of 82 parts sodium acetate, 120 parts water and 100 parts ice. The brownish-red solution is neutralized by dropwise addition of approximately 120 parts 30% aqueous sodium hydroxide. The product 2-(dimethylaminomethinimino)-4-chloro-5-formyl-thiazole can be separated by filtration. Alternatively, the product without isolation, can be reacted with 1 part piperidine and 6.6 parts malonic acid dinitrile in 20 parts ethanol. After stirring for about 3 hours at room temperature condensation is complete. The product of formula

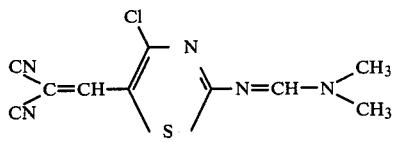
(b)

which is filtered off and washed, dyes polyester fibres in yellow fluorescent shades.

EXAMPLE 2

The mixture containing 2-(dimethylaminomethinimino)-4-chloro-5-formyl-thiazole prepared as described in Example 1 (without having been neutralized) is stirred for 2 hours at 50° whereby the compound of formula

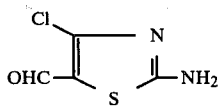

crystallizes out. The yellow product is filtered off after the suspension has cooled. The product can be used without further purification to prepare azo dyestuffs by diazotization and coupling with a coupling component.

EXAMPLE 3

Preparation of the compound of formula

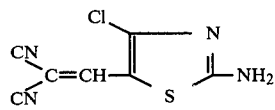

The aqueous suspension of 2-amino-4-chloro-5-formylthiazole prepared as described in Example 2 is adjusted to pH 5 with approximately 120 parts 30% aqueous sodium hydroxide, then 1 part piperidine and 6.6 parts malonic acid dinitrile in 20 parts ethanol are added thereto. Stirring is effected for 1 hour at room temperature and then 3 hours at 50°. The brown suspension is allowed to cool and the product is filtered off.

The product can also be produced in the following manner:

26.5 Parts of 2-(N,N'-dimethylaminomethinimino)-4-chloro-5-(2',2'-dicyanovinyl)-thiazole produced as described in Example 1 are suspended in 100 parts 50% sulphuric acid and stirred for approximately 18 hours at 50°. The mixture is left to cool and the product is filtered off.

Further compounds of formula II in which R is $NR_2R_3$ and m is 0, which can be produced in analogy with the procedures of Examples 1 to 3, are given in the following Table.

TABLE 1

| EX. No. | $R_1$ | $R_2$ | $R_3$ |
| --- | --- | --- | --- |
| 4 | —CH=N—OH | H | H |
| 5 | —CH=N—OH | | =CH—N(CH$_3$)$_2$ |
| 6 | —CH=N—NHC$_6$H$_5$ | H | H |
| 7 | —CHO | —C$_6$H$_4$m-(CH$_3$) | —C$_2$H$_5$ |
| 8 | " | —C$_6$H$_3$—3,4-Cl$_2$ | —CH$_3$ |
| 9 | " | H | —C$_6$H$_5$ |
| 10 | " | H | 2-naphthyl |
| 11 | —CN | H | H |
| 12 | —CHO | H | -Cyclohexyl |
| 13 | —CHO | —C$_2$H$_5$ | —C$_2$H$_5$ |
| 14 | —CHO | —CH$_3$ | —CH$_3$ |
| 15 | —CHO | —CH$_3$ | —C$_6$H$_5$ |
| 16 | —CHOCH$_2$CH$_2$O (cyclic) | H | H |
| 17 | —CH$_2$OH | H | H |
| 18 | —CH$_2$OCOCH$_3$ | H | H |
| 19 | —CH$_2$—OCH$_2$C$_6$H$_5$NO$_2$(p) | H | —CH$_2$C$_6$H$_4$—4NO$_2$ |
| 20 | —CHO | H | —CH$_2$CH=CH$_2$ |
| 21 | —CH=C—CO—NCH$_3$—CO—NCH$_3$—CO (cyclic) | | =C—N(CH$_3$)C$_6$H$_5$ |
| 22 | —CH=C(CN)CONH$_2$ | | =CH—N—(CH$_2$)$_4$CH$_2$ (cyclic) |

TABLE 1-continued

| EX. No. | $R_1$ | $R_2$ | $R_3$ |
|---|---|---|---|
| 23 | —CH=C(CN)CONHCONH$_2$ | | =CH—NH$_2$ |
| 24 | —CN | H | —C$_6$H$_5$ |
| 25 | —CN | H | 1-Naphthyl |
| 26 | —CHO | H | —C$_2$H$_5$ |
| 27 | —CHO | | =CH—N(CH$_3$)C$_6$H$_5$ |
| 28 | —CHO | | =CH—N—(CH$_2$)$_4$CH$_2$ (ring) |
| 29 | —HC=HC—CHO | | =CH—CH=CH—N(CH$_3$)$_2$ |
| 30 | —HC=HC—NO$_2$ | H | H |
| 31 | —HC=CH—CN | H | H |
| 32 | —HC=CH—COOH | H | H |
| 33 | —HC=CH—COOC$_2$H$_5$ | H | H |
| 34 | —HC=CH—COCH$_3$ | H | H |
| 35 | —CH=N—C$_6$H$_4$—(p)-NO$_2$ | H | H |
| 36 | —CH=N—C$_6$H$_5$ | | =CH—N(CH$_3$)$_2$ |
| 37 | CH=CH—C=CH—C[=C(CN)$_2$]CH$_2$C(CH$_3$)$_2$CH$_2$ | H | —CH$_3$ |
| 38 | —CH=C(CN)—COOCH$_2$C$_6$H$_5$ | H | H |
| 39 | —CH=C(CN)—SO$_2$—C$_6$H$_5$ | H | H |
| 40 | —CH=C(CN)COOC$_2$H$_4$CN | H | H |
| 41 | —CH=C(CN)COOCH$_2$COOC$_2$H$_5$ | H | H |
| 42 | —C=N—NH—C$_6$H$_3$-2,4-(NO$_2$)$_2$ | H | H |
| 43 | —CH=C(CN)COOCH$_3$ | H | H |
| 44 | —CH=C(CN)COOC$_2$H$_5$ | H | H |
| 45 | —CH=C(CN)$_2$ | | —(CH$_2$)$_5$— |
| 46 | " | | —(CH$_2$)$_2$—NCH$_3$—(CH$_2$)$_2$— |
| 47 | " | | —(CH$_2$)$_2$—O—(CH$_2$)$_2$— |
| 48 | " | H | —C$_6$H$_3$—2,4-(NO$_2$)$_2$ |
| 49 | —CH(OH)CN | H | H |
| 50 | —CHO | —CH$_2$CH$_2$OH | —C$_6$H$_5$ |
| 51 | —CHO | H | n-C$_4$H$_9$ |
| 52 | —CHO | —C$_6$H$_5$ | —C$_6$H$_5$ |
| 53 | —CHO | H | —C(CH$_3$)$_3$ |
| 54 | —CHO | H | —(CH$_2$)$_9$CH$_3$ |
| 55 | —CH=C(CN)$_2$ | H | —CH=C(CN)$_2$ |
| 56 | —CH=N—NH—CONH$_2$ | H | H |
| 57 | —CH=N—NHCSNH$_2$ | H | H |
| 58 | —CH=C(CN)CONHCH$_3$ | H | H |
| 59 | —CH=C(CN)CONHC$_6$H$_5$ | | =CH—N(CH$_3$)$_2$ |
| 60 |  —CH=C(CN)CON(piperidine) | | " |
| 61 | —CH=C(CN)COC$_6$H$_5$ | H | —C$_2$H$_5$ |
| 62 |  —CH=C(CN)CO$_2$-cyclohexyl | H | H |
| 63 | —CH=C(CN)SO$_2$CH$_3$ | —C$_2$H$_5$ | —C$_6$H$_5$ |
| 64 | 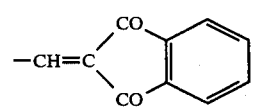 —CH=C(phthaloyl) | —CH$_3$ | —C$_6$H$_5$ |
| 65 | 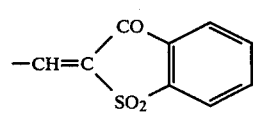 —CH=C(CO,SO$_2$-benzo) | —CH$_3$ | —C$_6$H$_5$ |

TABLE 1-continued

| EX. No. | R₁ | R₂ | R₃ |
|---|---|---|---|
| 66 | 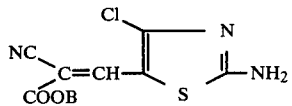 | H | —C₆H₅ |

In the following Table 2, further compounds of the invention of formula

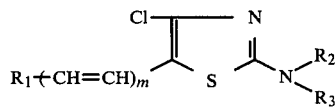

are given which may be prepared in analogy with the procedure of the foregoing Examples 1 to 3.

TABLE 2

| EX. No. | B |
|---|---|
| 67 | —CH₂CH₂Cl |
| 68 | —nC₃H₇ |
| 69 | —CH(CH₃)₂ |
| 70 | —CH₂CH₂CH₂Cl |
| 71 | —CH₂CH₂CH₂Br |
| 72 | —CH₂CH=CH₂ |
| 73 | —CH₂CBr=CH₂ |
| 74 | —CH₂CH=CHCl |
| 75 | —CH₂C≡CH |
| 76 | —CH₂CH₂COOC₂H₅ |
| 77 | —CH(CH₂OH)CH₂Cl |
| 78 | —CH(CH₂OCOCH₃)CH₂Cl |
| 79 | —CH₂CN |
| 80 | —CH₂C(CH₃)=CH₂ |
| 81 | —CH₂CH=CHCH₃ |
| 82 | —nC₄H₉ |
| 83 | —CH₂CH(CH₃)₂ |
| 84 | —CH₂CH₂—OCOC₂H₅ |
| 85 | —CH₂CHBrCH₃ |
| 86 | —nC₅H₁₁ |
| 87 | —nC₆H₁₃ |
| 88 | —CH₂C₆H₄(4-Cl) |
| 89 | —CH₂C₆H₄(4-NO₂) |
| 90 | —CH₂CHBrCOOCH₃ |
| 91 | —CH(CH₃)CH₂OCOCH₃ |
| 92 | —CH(C₂H₅)CH₂OH |
| 93 | —C(CH₃)₃ |
| 94 | —CH₂CH₂CHBrCH₃ |
| 95 | —CH₂CH₂CH₂CHBrCH₃ |
| 96 | —CH₂CHBrCH₂OH |
| 97 | —CH₂CHBrCOOH |
| 98 | —CH₂CBrCl₂ |
| 99 | —CH₂CH₂—OCONHC₂H₅ |
| 100 | —CH₂CH₂CH(CH₃)₂ |
| 101 | —CH₂CH₂CH=CH₂ |
| 102 | —CH₂CH₂OCOCH₃ |
| 103 | —CH₂CH₂COOH |
| 104 | —CH₂CH₂CH₂COOC₂H₅ |
| 105 | —CH₂CH₂OCOOCH₃ |
| 106 | —CH₂CH₂OC₆H₅ |
| 107 | —CH(CH₃)C₂H₅ |
| 108 | —CH₂CHOHC₂H₅ |
| 109 | —CH₂CH₂CH₂OCOCH₃ |
| 110 | —(CH₂)₉CH₃ |
| 111 | —CH₂COOCH₃ |
| 112 | —CH₂C(CH₃)₃ |
| 113 | —CH₂COOCH₂C₆H₅ |
| 114 | nC₈H₁₇ |
| 115 | —CH(COOC₂H₅)₂ |
| 116 | —CH₂CONH₂ |
| 117 | —CH(CH₃)CH₂CH₂CH₃ |
| 118 | —CH(CH₃)COOC₂H₅ |
| 119 | —CH₂CH₂CH₂C₆H₅ |
| 120 | —CH₂CONHC₆H₅ |

What is claimed is:

1. A compound of the formula,

in which

R₁ is -CHO, -CH=CR₄R₅, -CN, -CH=NOH, -CH₂OR₆, -CH=N-NHR₇, $$-CH=N-\underset{R_8}{\bigcirc}$$

or -CH(OH)CN,

R₂ is hydrogen; C₁₋₁₀alkyl; c₂₋₃alkyl substituted by hydroxy, cyano, chlorine, bromine, alkyl-C₁₋₂carbonyl, alkoxy-C₁₋₄carbonyloxy, alkylC₁₋₄carbonyloxy, alkylaminocarbonyloxy, dialkylaminocarbonyloxy, alkoxyC₁₋₄carbonyl, phenylaminocarbonyloxy or N-alkyl-N-phenylaminocarbonyloxy with the proviso that such substituted alkyl radicals are free from acetal groups; phenyl optionally substituted by 1 or 2 substituents selected from chlorine, bromine, methyl and nitro; alkenyl; dicyanoalkenyl; cyclohexyl; or naphthyl, and R₃ has one of the significances of R₂ with the proviso that when one of R₂ and R₃ is naphthyl the other has a significance other than naphthyl or phenyl, and when one of R₂ and R₃ is dicyanoalkenyl the other is hydrogen, or, R₂ and R₃ together with the nitrogen atom form a piperidine, piperazine or morpholine ring, or R₂ and R₃ together form a group of formula

=CH-(CH=CH)ₘ̄NR₁₀R₁₁ in which either,

R₁₀ is hydrogen or alkyl, and
R₁₁ is hydrogen, alkyl or phenyl,
or, R₁₀ and R₁₁ together with the N-atom form piperidine,
with the proviso that R₂ and R₃ are both hydrogen when R₁ is other than —CHO or —CH=CR₄R₅ and at least one of R₂ and R₃ is other than hydrogen when R₁ is —CH=CR₄R₅, either R₄ is hydrogen, cyano, alkylcarbonyl benzoyl, alkylsulphonyl, phenylsulphonyl, alkylaminocarbonyl, dialkylaminocarbonyl, phenylaminocarbonyl, N-alkyl-N-phenylaminocarbonyl, aminocarbonyl, aminocarbonylaminocarbonyl, piperidinylcarbonyl, aminothiocarbonyl, benzimidazolyl-2 or -COOB, in which B is hydrogen; C₁₋₁₀alkyl; C₅₋

7cycloalkyl; $C_{1-6}$alkyl substituted by up to three substituents selected from the group consisting of chlorine and bromine; $C_{1-6}$alkyl substituted by up to two substituents selected from the group consisting of chlorine, bromine, hydroxyl, cyano, phenoxy, alkoxy, carboxy, alkoxycarbonyloxy, alkylcarbonyloxy, alkoxycarbonyloxy, alkylaminocarbonyloxy, aminocarbonyl, alkylaminocarbonyl, phenylaminocarbonyl, benzyloxycarbonyl, and phenyl, in which the phenyl ring is optionally substituted by 1 or 2 substituents selected from chlorine, bromine and nitro, with the proviso that when such alkyl is substituted by a group containing a benzene ring it is monosubstituted and any substituted alkyl is free from acetal groups or B is $C_{3-6}$alkenyl optionally substituted by chlorine or bromine; or is alkynyl, and $R_5$ is hydrogen, cyano, alkoxycarbonyl, nitro or 3-di-cyanomethylene-5-5-dimethylcyclohene-1-yl with the proviso that when $R_5$ is the latter $R_4$ is hydrogen and when $R_5$ is nitro $R_4$ is hydrogen, methyl or ethyl, or $R_4$ and $R_5$ together form a ring system of the formula

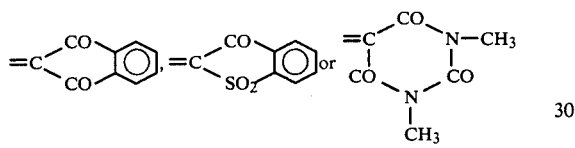

$R_6$ is hydrogen, alkyl, alkylcarbonyl or benzyl in which the benzene ring is optionally substituted by up to two substituents selected from chlorine, bromine and nitro, $R_7$ is hydrogen, alkyl, aminocarbonyl, amino thiocarbonyl or phenyl which is optionally substituted by 1 or 2 substituents selected from the group consisting of chlorine, bromine and nitro, $R_8$ is hydrogen, chlorine, bromine, methyl, $C_{1-2}$alkoxy, carboxyl, alkoxycarbonyl, cyano or nitro, m is 0 or 1, m' is 0 or 1, and any alkyl and alkoxy groups or moieties in such compounds contain 1 to 4 carbon atoms and any alkenyl or alkynyl groups or moieties 3 to 4 carbon atoms, except when otherwise stated.

2. A compound according to claim 1 in which $R_2$ is hydrogen; $C_{1-10}$ alkyl; $C_{2-3}$ alkyl substituted by hydroxy, cyano, chlorine, bromine, alkyl-$C_{1-2}$carbonyl, alkoxy-$C_{1-4}$carbonyloxy, alkyl-$C_{1-4}$carbonyloxy, alkylaminocarbonyloxy, dialkylaminocarbonyloxy, alkoxy-$C_{1-4}$carbonyl, phenylaminocarbonyloxy or N-alkyl-N-phenylaminocarbonyloxy with the proviso that such substituted alkyl radicals are free from acetal groups; phenyl optionally substituted by 1 or 2 substituents selected from chlorine, bromine, methyl and nitro; alkenyl; dicyanoalkenyl; cyclohexyl; or naphthyl, and $R_3$ has one of the significances of $R_2$ with the proviso that when one of $R_2$ and $R_3$ is naphthyl the other has a significance other than naphthyl or phenyl, and when one of $R_2$ and $R_3$ is dicyanoalkenyl the other is hydrogen, or $R_2$ and $R_3$ together form a group of formula =CH—(CH=CH)$_{m'}$NR$_{10}$R$_{11}$ $R_4$ is hydrogen, cyano, alkylcarbonyl, benzoyl, alkylsulphonyl, phenylsulphonyl, alkylaminocarbonyl, dialkylaminocarbonyl, phenylaminocarbonyl, N-alkyl-N-phenylaminocarbonyl, aminocarbonyl, aminocarbonylaminocarbonyl, aminothiocarbonyl, or —COOB, in which B is hydrogen; $C_{1-10}$alkyl; $C_{5-7}$cycloalkyl; $C_{1-6}$alkyl substituted by up to three substituents selected from the group consisting of chloride and bromine; $C_{1-6}$alkyl substituted by up to two substituents selected from the group consisting of chlorine, bromine, hydroxyl, cyano, phenoxy, alkoxy, carboxy, alkoxycarbonyl, alkylcarbonyloxy, alkoxycarbonyloxy, alkylaminocarbonyloxy, aminocarbonyl, alkylaminocarbonyl, phenylaminocarbonyl, benzyloxycarbonyl, and phenyl, in which the phenyl ring is optionally substituted by 1 or 2 substituents selected from chlorine, bromine and nitro, with the proviso that when such alkyl is substituted by a group containing a benzene ring, it is monosubstituted and any substituted alkyl is free from acetal groups; or B is $C_{3-6}$alkenyl optionally substituted by chlorine or bromine; or is alkynyl, and $R_5$ is hydrogen, cyano, alkoxycarbonyl, nitro or 3-di-cyanomethylene-5-5-dimethylcyclohexen-1-yl with the provisos that when $R_5$ is the latter $R_4$ is hydrogen and when $R_5$ is nitro $R_4$ is hydrogen, methyl or ethyl, $R_{10}$ is hydrogen or alkyl, and $R_{11}$ is hydrogen, alkyl or phenyl.

3. A compound according to claim 2 wherein $R_1$ is $R_1'$, where $R_1'$ is —CHO, —CH=CR$_4$R$_5$, —CH=NOH or CN, $R_2$ is $R_2'$, where $R_2'$ is hydrogen, $C_{1-4}$alkyl, hydroxyethyl, cyanoethyl or phenyl, $R_3$ is $R_3'$, where $R_3'$ is hydrogen, $C_{1-4}$alkyl, allyl, cyclohexyl, or naphthyl, or $R_2'$ and $R_3'$ form a group of formula =CH(CH=CH)$_{m'}$NR$_{10}$R$_{11}$, where $R_{10}$ and $R_{11}$ are $C_{1-4}$alkyl, $R_4$ is $R_4'$, where $R_4'$ is cyano; benzoyl; methylsulphonyl; phenylsulphonyl; methyl or ethylaminocarbonyl; phenylaminocarbonyl; aminocarbonyl; aminocarbonylaminocarbonyl; or —COOB', where B' is $C_{1-10}$alkyl, cyclohexyl, $C_{1-6}$alkyl substituted by up to two substituents selected from the group consisting of chlorine, bromine, hydroxy, cyano, $C_{1-2}$alkoxy, carboxy, alkoxy($C_{1-2}$)carbonyl, alkyl($C_{1-2}$)carbonyloxy, $C_{1-2}$alkoxycarbonyloxy, $C_{1-2}$alkylaminocarbonyloxy, aminocarbonyl, phenylaminocarbonyl, benzyloxycarbonyl, phenyl, chlorophenyl, nitrophenyl, with the proviso that when such alkyl is substituted by a group containing a benzene ring, it is monosubstituted and any substituted alkyl is free from acetal groups or B' is alkenyl optionally substituted by chlorine or bromine or is alkynyl, and $R_5$ is $R_5'$, where $R_5'$ is cyano, nitro or 3-dicyanomethylene-5,5-dimethylcyclohexen-1-yl with the proviso that when $R_5'$ is any one of the latter two significances, $R_4$ is hydrogen.

4. A compound according to claim 1, in which m and m' are both 0.

5. A compound according to claim 1, in which any $C_{1-4}$alkyl group or moiety in $R_4$ contains 1 or 2 carbon atoms.

6. A compound according to claim 4, in which $R_2$ is $R_2'$, where $R_2'$ is hydrogen, $C_{1-4}$alkyl, hydroxyethyl, cyanoethyl or phenyl and $R_3$ is $R_3'$, where $R_3'$ is hydrogen, $C_{1-4}$alkyl, allyl, cyclohexyl, naphthyl or phenyl, or $R_2'$ and $R_3'$ together form a group of formula $=CHNR_{10}R_{11}$, where $R_{10}$ and $R_{11}$ are $C_{1-4}$alkyl.

7. A compound according to claim 6, in which when $R_3'$ is cyclohexyl or phenyl, $R_2'$ is other than phenyl and when $R_3'$ is naphthyl $R_2'$ is hydrogen.

8. A compound according to claim 4, in which $R_1$ is $R_1'$, where $R_1'$ is —CHO, —CH=CR$_4$R$_5$, —CH=NOH or CN.

9. A compound according to claim 7, in which $R_1$ is —CHO or —CH=CR$_4$R$_5$.

10. A compound according to claim 9, in which $R_4$ is $R_4'$, where $R_4'$ is cyano; benzoyl; methylsulphonyl; phenylsulphonyl; methyl or ethylaminocarbonyl; phenylaminocarbonyl; aminocarbonyl; aminocarbonylaminocarbonyl; piperidinylcarbonyl; benzimidazolyl-2 or —COOB', where B' is $C_{1-10}$alkyl, cyclohexyl, $C_{1-6}$alkyl substituted by up to two substituents selected from the group consisting of chlorine, bromine, hydroxy, cyano, $C_{1-2}$alkoxy, carboxy, alkoxy($C_{1-2}$)carbonyl, alkyl($C_{1-2}$)carbonyloxy, $C_{1-2}$alkoxycarbonyloxy, $C_{1-2}$alkylaminocarbonyloxy, aminocarbonyl, phenylaminocarbonyl, benzyloxycarbonyl, phenyl, chlorophenyl, nitrophenyl, with the proviso that when such alkyl is substituted by a group containing a benzene ring it is monosubstituted and any substituted alkyl is free from acetal groups; or B' is alkenyl optionally substituted by chlorine or bromine or is alkynyl. and $R_5$ is $R_5'$, where $R_5'$ is cyano, nitro or β-(3-dicyanomethylene-5,5-dimethylcyclohexen-1-yl)vinyl with the proviso that when $R_5'$ is any one of the latter two significances $R_4$ is hydrogen.

11. A compound according to claim 9, in which $R_1$ is $R_1'''$, where $R_1'''$ is —CHO or —CH=C(CN)R$_4''$, where $R_4''$ is cyano, alkoxy($C_{1-6}$)carbonyl, benzoyl, cyclohexyloxycarbonyl, $C_{3-4}$-alkenyloxycarbonyl, chloro- or bromo$C_{3-4}$alkenyloxycarbonyl or alkoxy($C_{1-6}$)carbonyl in which the alkyl group is substituted by up to two substituents selected from the group consisting of chlorine, bromine, hydroxyl phenyl, carboxy, alkoxy$C_{1-2}$carbonyl, alkyl($C_{1-2}$)carbonyloxy, $C_{1-2}$alkylaminocarbonyloxy, alkoxy$C_{1-2}$carbonyloxy.

12. A compound according to claim 11, in which $R_2'$ and $R_3'$ are both hydrogen or $R_2'$ and $R_3'$ together form =CH—N(CH$_3$)$_2$.

13. A compound according to claim 1, in which m is 0.

14. A compound according to claim 12 of formula

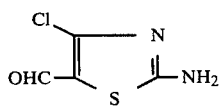

15. A compound according to claim 12 of formula

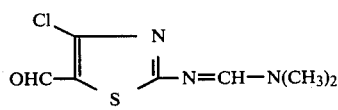

16. A compound according to claim 1, in which $R_2$ and $R_3$ have a significance other than together forming a heterocyclic ring and $R_4$ and $R_5$ have a significance other than forming a carbocyclic or heterocyclic ring system.

17. A compound according to claim 16, in which m and m' are 0.

18. A compound according to claim 1 of the formula

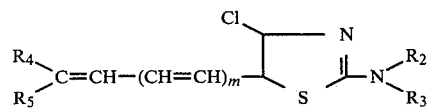

in which one of $R_2$ and $R_3$ is other than hydrogen.

19. A compound according to claim 1 wherein
$R_1$ is —CHO, —CH=CR$_4$R$_5$, —CH—NOH, —CH$_2$OR$_6$, —CH=N—NHR$_7$,

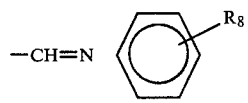

or —CH(OH)CN.

20. A compound according to claim 4, wherein
$R_1$ is —CHO, —CH=CR$_4$R$_5$, —CH—NOH, —CH$_2$OR$_6$, —CH=N—NHR$_7$,

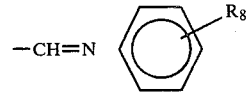

or —CH(OH)CN.

21. A compound according to claim 6, in which
$R_1$ is —CHO, —CH=CR$_4$R$_5$, —CH—NOH, —CH$_2$OR$_6$, —CH=N—NHR$_7$,

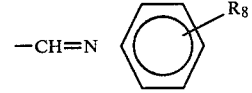

or —CH(OH)CN.

22. A compound according to claim 6, in which
$R_1$ is —CHO or —CH=CR$_4$R$_5$.

23. A compound according to claim 16, wherein
$R_1$ is —CHO, —CH=CR$_4$R$_5$, —CH—NOH, —CH$_2$OR$_6$, —CH=N—NHR$_7$,

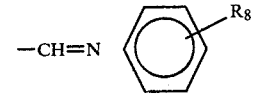

or —CH(OH)CN.

24. A compound according to claim 16, wherein
$R_1$ is —CHO or —CH=CR$_4$R$_5$.

25. A compound according to claim 2, wherein $R_1$ is —CHO, —CH=$CR_4R_5$, —CH—NOH, —CH$_2OR_6$, —CH=N—$NHR_7$,

or —CH(OH)CN.

26. A compound according to claim 2, wherein $R_1$ is —CHO or —CH=$CR_4R_5$.

27. A compound according to claim 3, wherein $R_1$ is —CHO or —CH=$CR_4R_5$.

28. A process for the production of a compound, as defined in claim 1 and in which $R_1$ is formyl, comprising reacting a compound of formula

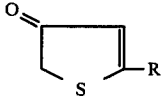

or a salt thereof,
with a Vilsmeier complex comprising a formamide and an acid chloride, and optionally hydrolytically converting an imino group as R to a primary amine.

29. A process according to claim 28, in which the Vilsmeier complex comprises phosphorousoxychloride and dimethylformamide.

* * * * *